United States Patent
Parker, Jr.

(10) Patent No.: US 8,649,880 B1
(45) Date of Patent: Feb. 11, 2014

(54) DEPLOYABLE STIMULATOR ARRAY AND METHOD OF USE

(76) Inventor: Autry J. Parker, Jr., Memphis, TN (US)

(*) Notice: Subject to any disclaimer, the term of this patent is extended or adjusted under 35 U.S.C. 154(b) by 0 days.

(21) Appl. No.: 13/526,089

(22) Filed: Jun. 18, 2012

Related U.S. Application Data

(60) Provisional application No. 61/544,359, filed on Oct. 7, 2011.

(51) Int. Cl.
*A61N 1/00* (2006.01)
*A61B 5/04* (2006.01)

(52) U.S. Cl.
USPC .......................... 607/116; 600/374; 600/393

(58) Field of Classification Search
USPC ................... 600/374, 393; 607/116
See application file for complete search history.

(56) References Cited

U.S. PATENT DOCUMENTS

| | | | |
|---|---|---|---|
| 4,379,462 A | 4/1983 | Borkan et al. | |
| 6,161,047 A | 12/2000 | King et al. | |
| 6,415,187 B1 | 7/2002 | Kuzma et al. | |
| 7,191,018 B2 | 3/2007 | Gielen et al. | |
| 7,613,524 B2 | 11/2009 | Jordan | |
| 2005/0203600 A1 | 9/2005 | Wallace et al. | |
| 2005/0251239 A1 | 11/2005 | Wallace et al. | |
| 2009/0171274 A1* | 7/2009 | Harlev et al. | 604/95.04 |

* cited by examiner

*Primary Examiner* — Nicole F Lavert
(74) *Attorney, Agent, or Firm* — Harris, Shelton, Hanover & Walsh; Susan B Fentres

(57) ABSTRACT

This invention provides a percutaneous implantable electrode array that can be deployed or repositioned though a needle insertion site. The deployable electrode apparatus, in one embodiment, is made of a fixed electrode array on a central body of the apparatus and a deployable electrode array. The deployable electrode array is actuated by at least two struts, each of the struts having a first and second end. The central body of the apparatus is configured to retain the first end of the at least two struts. Each of the side arrays are flexurally connected to the second end of each of the strut and the side arrays are connected to at least one stylet, which extends to the proximal end of the apparatus.

7 Claims, 14 Drawing Sheets

SECTION A-A

DEPLOYABLE STIMULATOR ARRAY AND METHOD OF USE

RELATED PATENT APPLICATIONS

This patent application claims the benefit of U.S. provisional patent application Ser. No. 61/544,359 under 35 USC sec 119 (e) (hereby specifically incorporated by reference).

BACKGROUND OF THE INVENTION

The present invention relates to a deployable stimulator array and a method to non-surgically implant, deploy and remove the lead. This invention provides a stimulator made of a plurality of electrodes that can be implanted in the body and adjusted through percutaneous placement. More specifically, this invention relates to implantable leads that combine the features of a percutaneous lead with those of a paddle lead, to provide better electrical stimulation, but still allow delivery through percutaneous placement.

A spinal cord stimulator is a well established medical device used to exert pulsed electrical signals to the spinal cord for treatment of chronic pain and movement disorders. Currently, two types of designs of spinal cord stimulators are used by physicians. The leads/electrodes consist of an array of leads that are either percutaneous type or paddle type. The percutaneous type utilizes percutaneous placement of single or multiple linear cylindrical electrodes with variable numbers of contacts, whereas the paddle type uses surgically implanted paddle style electrodes with flat columns of contacts.

Percutaneous type electrodes are easier to insert in comparison with paddle type electrodes, which are inserted via an incision over the spinal cord. Percutaneous electrodes have the advantage of ease of placement, but also have disadvantages including current inefficiency, migration and coverage limitations. Paddle leads have efficiencies of unidirectional current and the ability to provide arrays for better coverage but require invasive surgery for placement and removal.

BRIEF SUMMARY OF THE INVENTION

The present invention overcomes these limitations by providing a deployable stimulator array that combines the advantages of percutaneous electrodes and paddle electrodes. It works not only as a percutaneous electrode by minimizing the size of the incision during insertion, but also as a paddle type electrode by providing greater efficiency and better electrical coverage.

This invention combines the features of a percutaneous lead with those of a paddle lead, to provide better electrical stimulation, but to still allow delivery of the deployable stimulator array through a Tuohy needle. This invention provides a percutaneous implantable electrode array that can be deployed or repositioned though a needle insertion site. The apparatus of this invention is made of a lead having multiple arrays; some of the electrode arrays are deployable, while other electrodes are stationary.

This expandable multiple stimulator array apparatus includes a first fixed electrode array and a second deployable electrode array. The implantable lead apparatus is positioned by a removable mid-line stylet. Furthermore, the deployable electrode array is actuated by an actuator assembly.

In the present invention, the actuator assembly is made of at least two struts, each of the struts having a first and a second end. The central body of the apparatus is configured to retain the first end of each of the at least two struts. Additionally, the actuator assembly includes at least two side electrode arrays; each of the side electrode arrays is flexurally connected to the second end of each of the struts. At least one stylet is connected to the at least two side electrode arrays. The stylet extends to the proximal end of the apparatus to allow for control by the clinician.

In another embodiment, an apparatus with more than one set of struts is provided. In this embodiment, the plurality of first struts is retained in the central body at a first position and a second plurality of struts is retained in the central body at a second position. This configuration provides a larger electrical field.

This invention also provides a method to actuate the deployable electrode apparatus positioned in situ by moving the side stylets relative to the fixed electrode array on the central body of the apparatus. Furthermore, this invention also provides a method to alleviate pain in a spinal canal by inserting the deployable electrode apparatus into a spinal canal, positioning the apparatus, deploying the deployable electrode array, removing the mid-line stylet and providing electrical stimulation to the apparatus.

BRIEF DESCRIPTION OF THE SEVERAL VIEWS OF THE DRAWING

For a fuller understanding of the nature and desired objects of the present invention, reference is made to the following detailed description taken in conjunction with the accompanying drawing figures wherein:

FIG. 11 shows a view illustrating the position of the deployable electrode apparatus into a patient's spine in the expanded from.

DETAILED DESCRIPTION OF THE INVENTION

Figure 1:
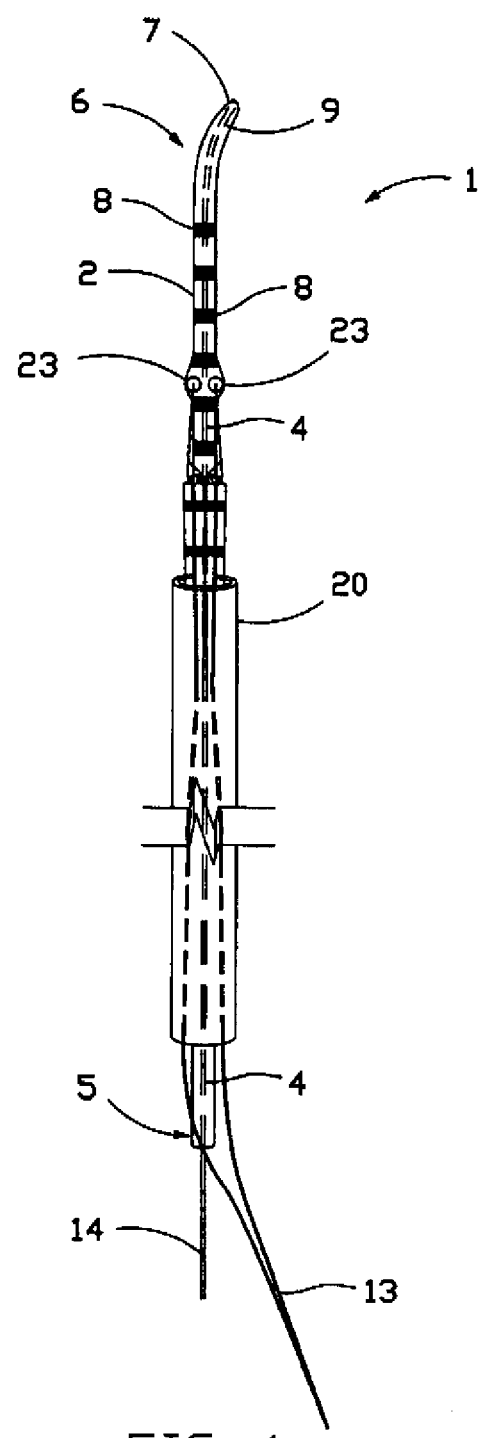
FIG. 1 shows a perspective view of a first embodiment of a deployable electrode apparatus in a retracted form.
Figure 2:
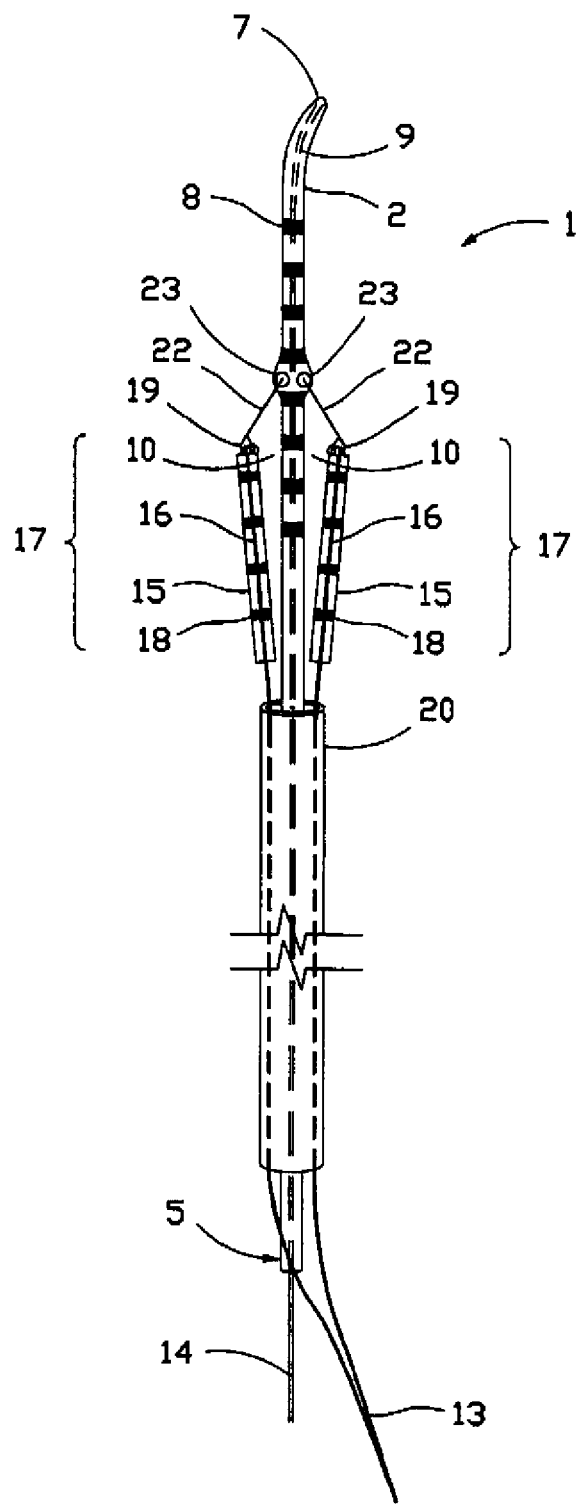
FIG. 2 shows a perspective view of a first embodiment of a partially expanded deployable electrode apparatus.

Now referring to FIGS. 1-3, a deployable electrode apparatus 1 is shown. The deployable electrode apparatus 1 is made of a lead having multiple electrode arrays. Certain of the arrays are deployable, while other electrodes are fixed with respect to the central body 2 of the lead. In FIG. 1, the deployable electrode apparatus 1 is in the retracted form, while in FIG. 3A the deployable electrode apparatus 1 is in the deployed form. The deployable electrode apparatus 1 is connected to a therapy delivery device (not shown) by wire connections shown in FIG. 11 at 49 to provide the required amount of electrical stimulation for a particular therapy.

The deployable electrode apparatus 1 is made of a central body 2 having a plurality of electrodes. In the preferred embodiment, the central body 2 is elongated and made of a substantially flexible plastic or elastomeric tube, such as silicone or vinyl, which fits within the outer sheath 20 along with the bundles or groups of electrical leads shown in FIG. 11 at 49.

In the retracted form, the deployable electrode apparatus 1 is sized to fit within a 14 gauge Tuohy needle. The needle (not shown) can pass through skin and deliver the deployable electrode apparatus 1 to the epidural space in a patient's spinal canal. The diameter of deployable electrode apparatus 1 when retracted is not more than 1.6 mm to fit within a 14 gauge Tuohy needle.

The central body 2 has a proximal end 5 and distal end 6. The central body 2 accommodates a mid-line stylet 4. A stylet is a wire-like device made of metal such as stainless steel or other suitable metal which provides stiffness for directional control during device insertion in the epidural space and deployment control during device operation. The proximal end 14 of the mid-line stylet 4 is attached to the clinician's control device (not shown) and the distal end 9 is inserted in the central body 2 for directional control of the tip 7 of the deployable electrode apparatus 1 during insertion into the patient. The mid-line stylet 4 is used to guide the deployable electrode apparatus 1 to its operational site. The mid-line stylet 4 is not fixedly connected, i.e. it is reversibly connected to the central body 2 and is removed once the deployable electrode apparatus 1 is placed in the patient.

The deployable electrode apparatus 1 further includes a fixed electrode array 8 mounted on or integrally formed on the central body 2 on the distal end 6 of the deployable electrode apparatus 1. The electrodes of the fixed electrode array 8 can be formed on to the central body 2 using known deposition processes and are composed of an electro-conductive material. The fixed electrode array 8 is preferably of the percutaneous style i.e. conductive bands 360° around the central body 2 circumference and preferably includes eight electrodes. For example, electrodes of the fixed electrode array 8 are metalized patches deposited on the surfaces of the elongated body 2 for electrical contact with the patient's tissues (not shown). Each electrode or patch is connected by an electrical lead to the proximal end (clinician's end) where they are attached to an electrical control device (not shown). Leads are bundled together or several electrodes (patches) may be multiplexed into a fewer number of conductive leads to conserve space.

The deployable electrode apparatus 1 further includes a plurality of side electrode arrays 17. The side electrode arrays 17 includes a plurality of side-electrodes 18 that are preferably flat and are positioned or attached to an electrical support member 15, such as a rigid plastic material. The plurality of side-electrodes 18 can include a membrane 10 of flexible material that is connected to the central body 2 and support member 15 to form a surface suitable to support side-electrodes 18 mounted on or integrally formed on the membrane 10 of the distal end 6 of the deployable electrode apparatus 1. The electrodes of the side electrode 18 can be formed on to membrane 10 using known deposition processes and are composed of an ejectro-conductive material.

Each of the side electrode arrays 17 are permanently connected to a side stylet 16. A stylet is a thin flexible member used to guide the side arrays 17. The side stylet 16 can be made of plurality of individual stylets or a single stylet with separate branches. The side stylet 16 continues to the proximal end 13 where they are attached to a control device (not shown). In one embodiment, the side stylet 16 is free (loose) within the outer sheath 20 and in another embodiment the side stylet 16 is attached to the inner wall or embedded within the walls of the outer sheath 20. If a plurality of individual stylets 16 is used, they can be joined 13 for ease of operation.

Now referring to FIGS. 3A-D, the deployable electrode array 1 includes an actuator assembly 32 as shown. The term actuator assembly relates to all of the structural elements that move or actuate the side electrode array 17. The term actuator refers to either retracting or deploying the side electrode array 17. The actuator assembly 32 actuates the plurality of side arrays 17. In one embodiment, the actuator assembly 32, for the side arrays 17 includes at least two struts 22. Each strut 22 has a first end 40 and a second end 41. The first end 40 is configured to be retained by the central body 2. An opening 45 is provided in central body 2 of sufficient diameter to retain the first end 40 of the strut 22. In one embodiment the struts 22 are metal with a nonmetal coating. In this configuration the first end 40 includes a thickening of the strut material on the first end 40, so that strut 22 can be retained within central body 2. This element is a retention member 23. The retention member 23 can be reinforceably retained within the wall central body 2 from pulling out with a washer 46. The washer 46 is positioned between the retention member 23 and the central body 2.

Figure 3A:
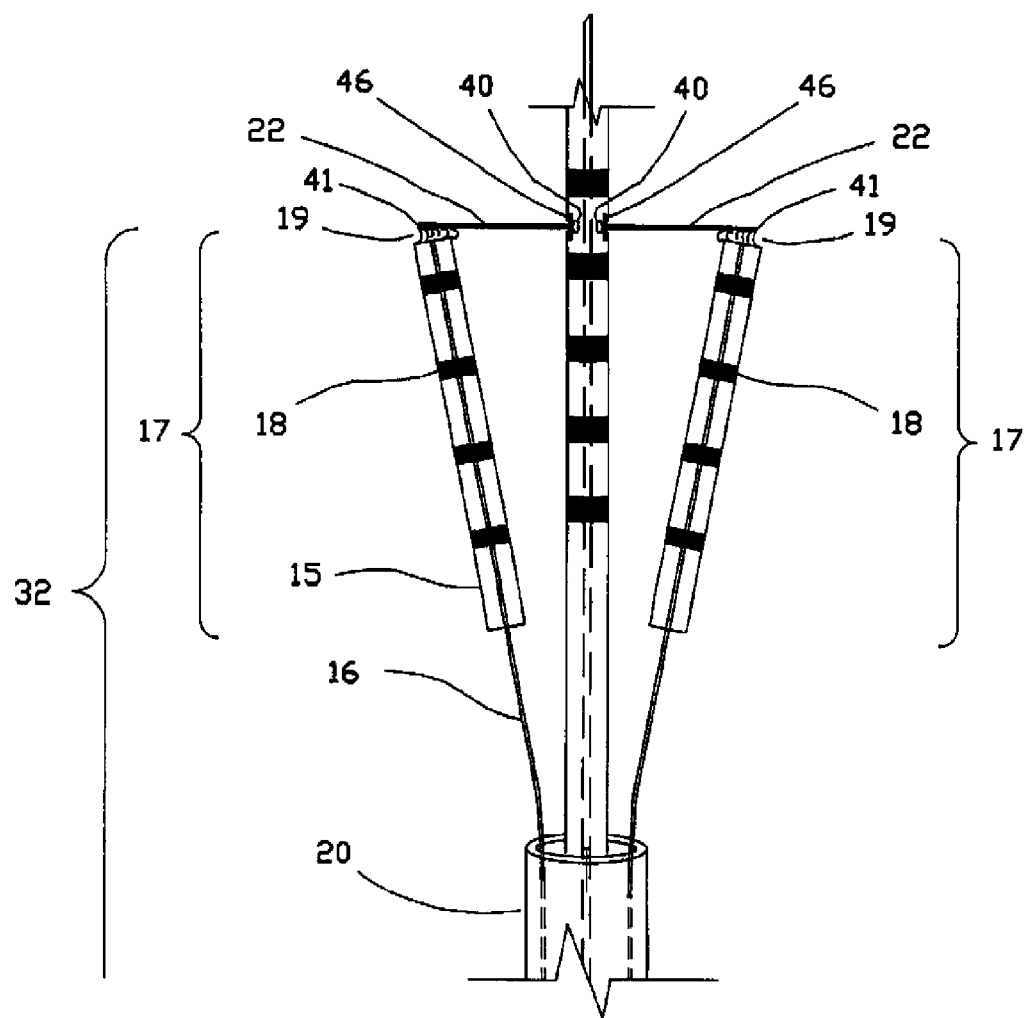
FIG. 3A shows a perspective view of a first embodiment of the actuator assembly.
Figure 3B:
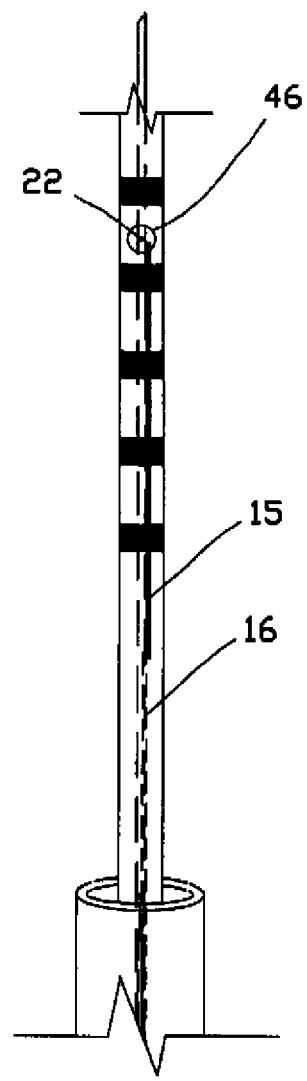
FIG. 3B shows a partial side view of an embodiment of the actuator assembly.
Figure 3C:
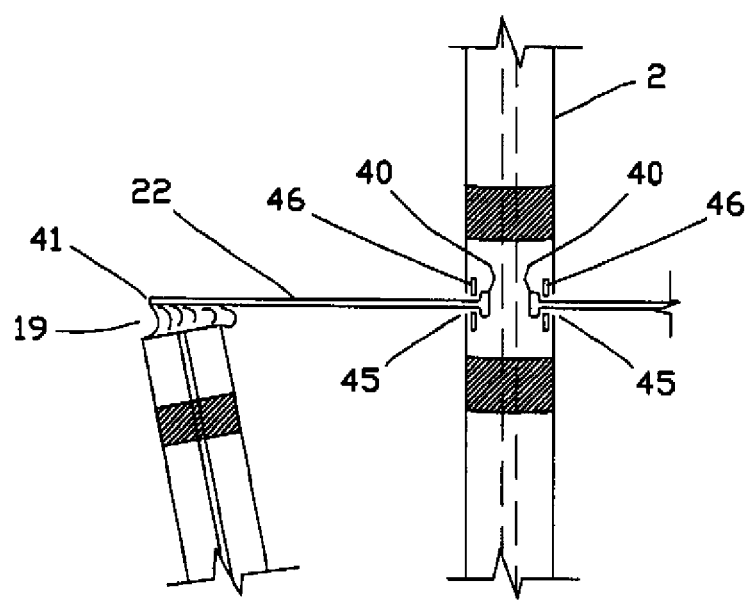
FIG. 3C shows a partial side view of an embodiment of the actuator assembly.
Figure 3D:
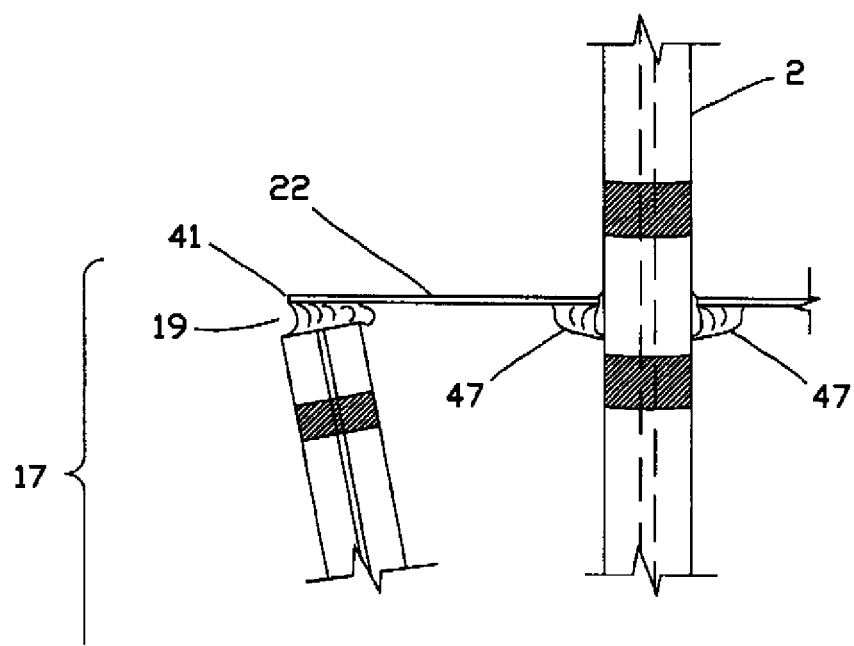
FIG. 3D shows a partial side view of an embodiment of the actuator assembly.

In an alternative embodiment shown in FIG. 3D, the struts 22 can be attached to the central body 2 by means of a ligament or strip of flexible material 47, which allows the struts 22 to rotate upward or downward.

The struts 22 are made of a material that is sufficiently stiff to maintain the swing radius as the side electrode arrays 17 are deployed. The desired swing radius, ie degree of rotation is between 70-110 degrees, but preferably between 80-90 degrees of rotation between the central body 2 and side array 17.

Each of the side electrode arrays 17 are non-reversibly flexurally connected to the struts 22 by a flexural connection member 19. A flexural connection means that the connector element 19 deforms as it bends. The flexural connector 19 is a flexible material which keeps the end of the side electrode 17 close to the end of the strut 22 as the side electrode is actuated. Examples of suitable flexible connectors include elastomeric materials, such as polyurethane and silicone rubber. The flexural connection member 19 is attached to the side arrays 17 by common attachment means such as heat sealing or bonding and flexural connection member 19 is attached by common attachment means such as heat sealing or bonding, to the struts 22.

The side stylets 16 extend to the proximal end 5 of the deployable electrode apparatus 1. The deployable electrode apparatus 1 includes outer sheath 20 which surrounds a portion of deployable electrode apparatus 1 and retains the deployable electrode apparatus 1 in the retracted state. The outer sheath 20 is a fairly flexible plastic tube, such as silicone or vinyl, which contains all the deployable electrode apparatus 1.

Figure 4:
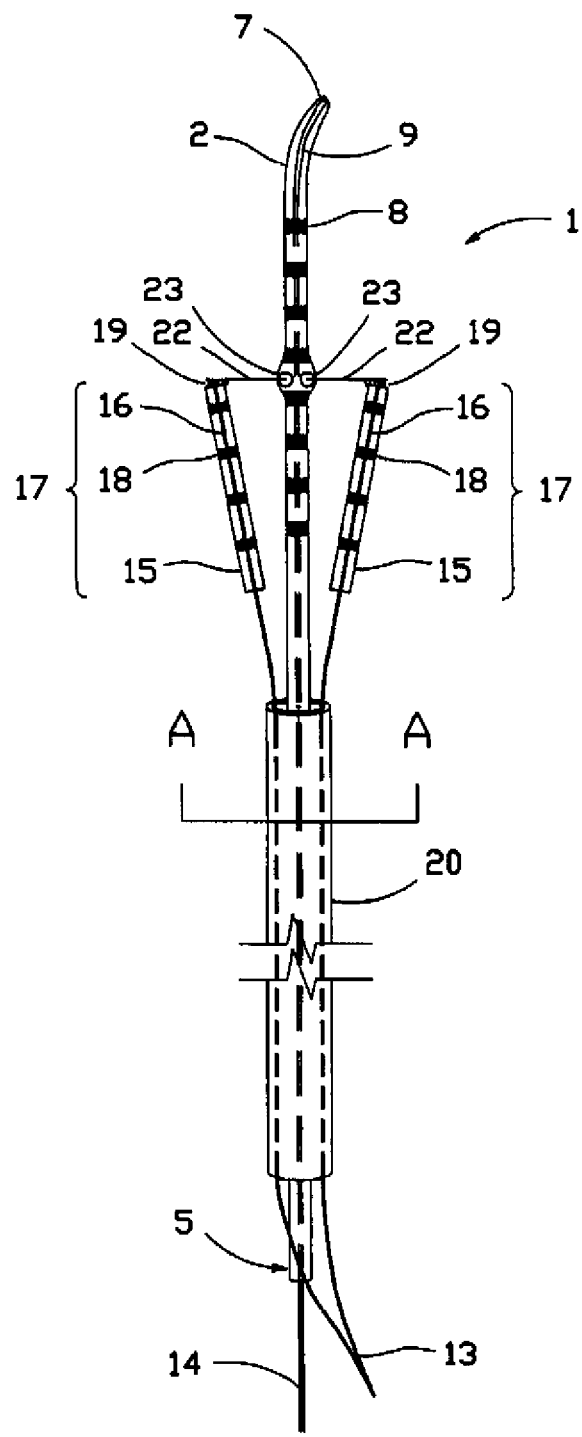
FIG. 4 shows a perspective view of a first embodiment of a deployable electrode apparatus with a cross-section taken at A-A.
Figure 5:
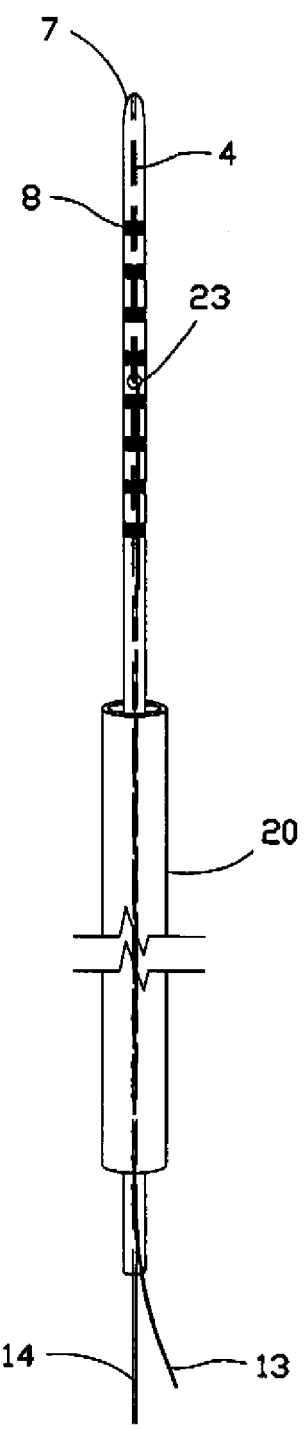
FIG. 5 shows a side view of the first embodiment of the invention.

Now referring to FIGS. 4-5, after positioning the deployable electrode apparatus 1 in the target location, such as in the patient's epidural space, the side arrays 17 are deployed from sheath 20. The side electrode arrays 17 are deployed or retracted by an actuator assembly 32. The actuator assembly 32 is manipulated by the side stylets 16. The side stylets 16 are disposed through the open proximal end 5 of the central body 2 to connect to a control device (not shown). These elements form an actuator assembly 32 that can be used to actuate the side electrode arrays 17. The sheath 20 is configured to retain the side electrode arrays 17 in the retracted form. Each of the side stylets 16 are fixedly connected to the struts 22 by one of a plurality of flexural connectors 19 and are thus not removable.

The electrodes 18 on the side electrode arrays 17 are actuated by manipulating the non-removable side stylet 16 relative to the fixed electrode array 8 on the central body 2. The side electrode array 17 is deployed by manipulating the side stylets 16 with respect to fixed electrode array 8 on the central body 2. The deployable electrode apparatus 1 can be removed by holding the side stylet 16 and retracting the central body 2. In this way the struts 22 are advanced further distally (retracted), such that the side stylet 16 folds along the fixed electrode array 8 in the stowed position as shown in FIG. 1. In this configuration, the deployable electrode apparatus 1 can be more easily removed from the spinal space.

Now referring to FIGS. 4-7, in an alternative embodiment, the first end 40 is connected to a retention member 23, such as micro beads. The micro beads can be positioned to bisect the fixed electrode array 8. Further, the micro bead can be reinforceably retained within the wall central body 2 from pulling out with a washer 46. Additionally, the walls of the central body 2 can be curved to accommodate the plurality of retention members 23 such as micro beads. In this embodiment, the struts 22 function like a lever, while the edge of the central body 2 functions like a fulcrum to provide a rocking motion for the plurality of side electrode arrays 17. The wall of the central body 2 is somewhat compliant, allowing the struts 22 to slightly deform the sidewall of the central body 2, where the side stylets 16 come through and rock from the stowed position as shown in FIG. 1 to deployed position as shown is FIG. 3A. This connection provides mechanical integrity to the actuator assembly 32. The wall of the central body 2 is somewhat compliant, allowing the struts 22 to slightly deform the sidewall of the central body 2, where the side stylets 16 come through and rock from the stowed position as shown in FIG. 1 to deployed position as shown is FIG. 3A.

The side stylets 16 remain in the deployable electrode apparatus 1 for subsequent adjustment and/or repositioning of side-array of electrodes 18 and for returning the side-array of electrodes 18 to the central body 2 for removal of the deployable electrode apparatus 1 through the Tuohy needle. The struts 22 are attached to the side walls 42 of the central body 2 by means of passing through an opening 45 in the wall 42 of the central body 2, and are retained from pulling out by an enlarged medial end 40 of each of the struts 22. The struts 22 rock up and down to effect deployment.

If the stylet 16 is free (loose) within the outer sheath 20, then the procedure to position the deployable electrode apparatus 1 includes the steps of positioning the central body 2 as desired with the mid-line stylet 4. Then the clinician holds the outer sheath 20 steady and pulls the central body 2 to deploy the plurality of side array 17. If the clinician wishes to retract the plurality of side arrays 17, the clinician continues to pull the central body 2 until the struts 22 have rotated upward and the plurality of side electrodes 18 are against either side of the central body 2 as shown in FIG. 1. In one embodiment, the side stylet 16 is connected to the electrical support member 15. In another embodiment the side stylet 16 runs the length of the side electrode arrays 17. In this embodiment, the side stylet 16 is preferably wrapped in an electrical insulator.

Figure 6:
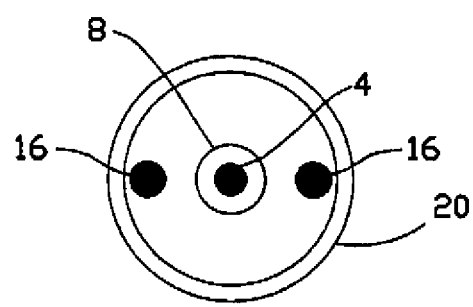
FIG. 6 shows a cross-section view of the first embodiment of the invention taken at A-A.

Now referring to FIG. 6 a cross sectional view of the first embodiment is shown. In this embodiment, a mid-line stylet 4 is surrounded by a fixed electrode array 8. The side stylet 16 is shown surrounded by the sheath 20.

Figure 7:
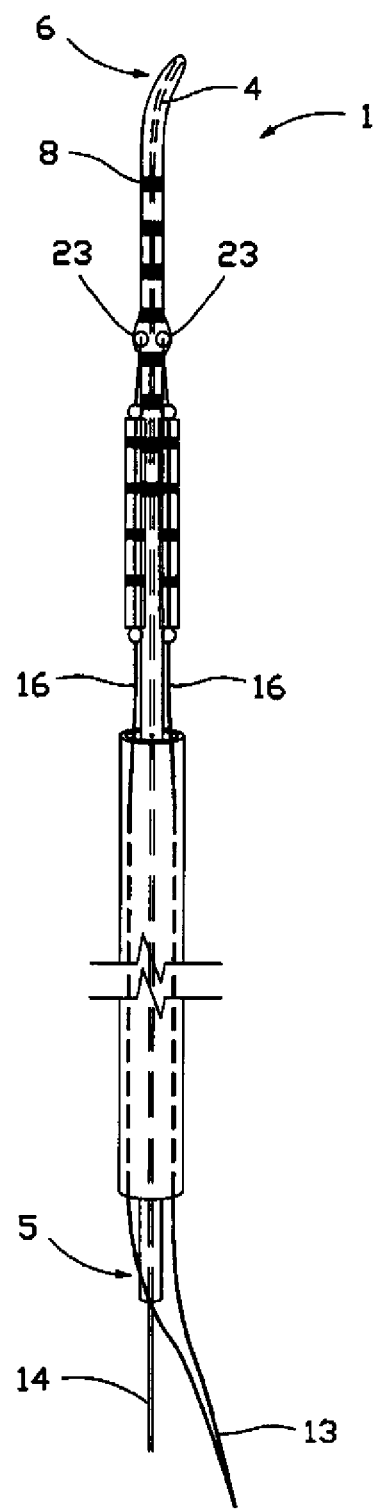
FIG. 7 shows a perspective view of a second embodiment of a deployable electrode apparatus in the retracted form.
Figure 8:
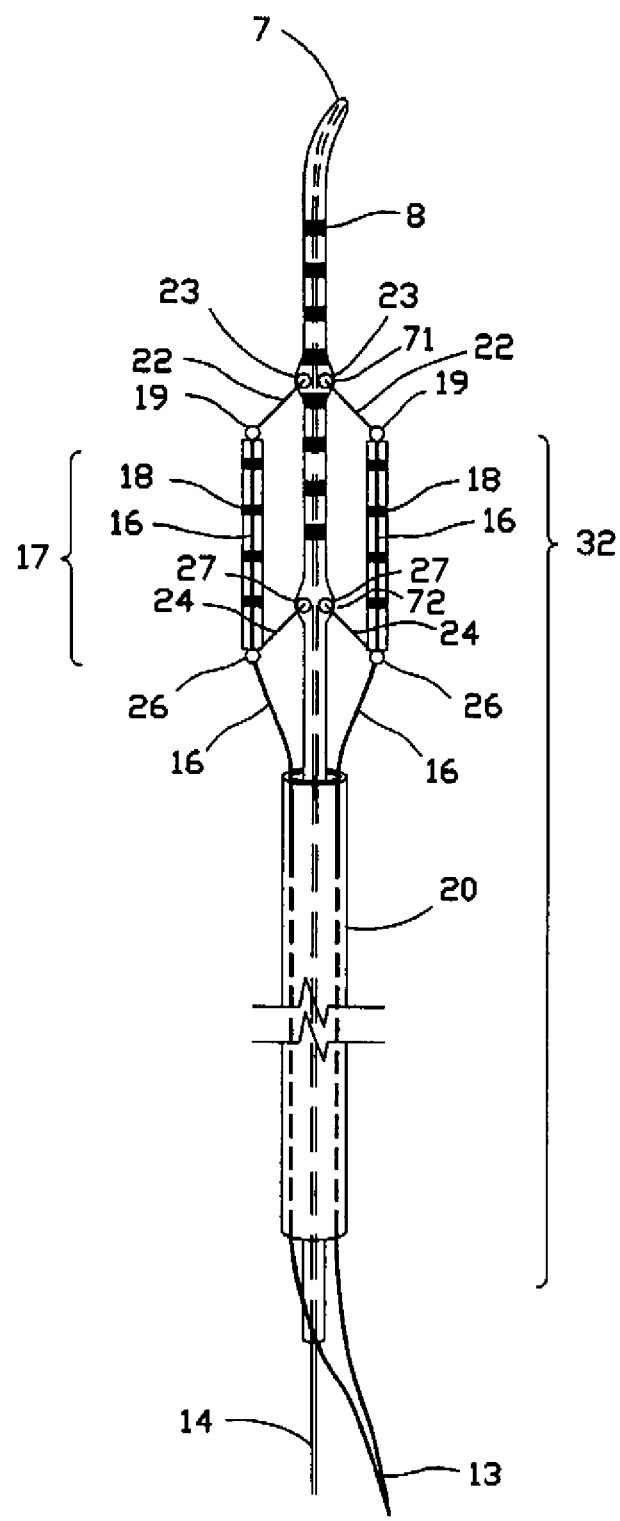
FIG. 8 shows a perspective view of a second embodiment of a partially expanded deployable electrode apparatus.
Figure 9:
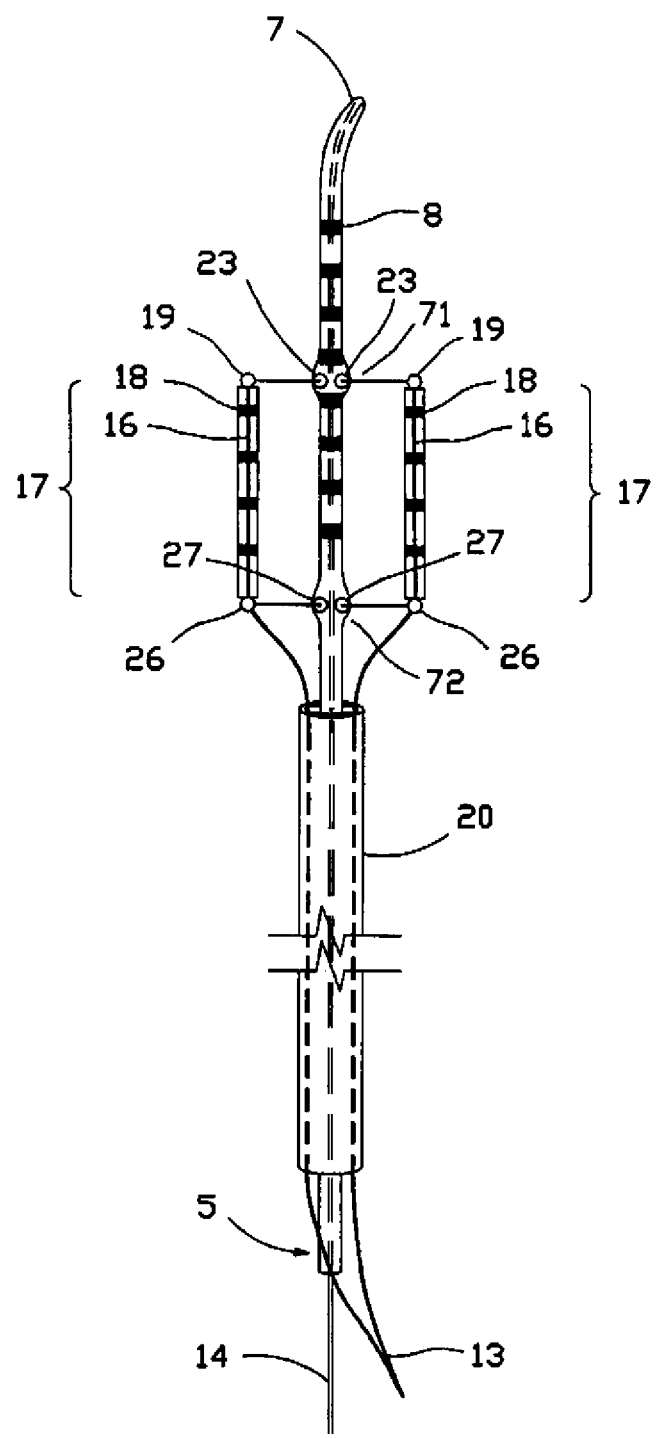
FIG. 9 shows a perspective view of a second embodiment of an expanded deployable electrode apparatus.

Now referring to FIGS. 7-9 another embodiment is shown. The advantage of this embodiment is that it provides a wider influence over the target tissue. In this embodiment, a deployable electrode apparatus 1 with more than one set of struts is provided. This includes a plurality of first struts 22 and a plurality of second struts 24. The central body 2 is configured to retain a portion of the first struts 22 or in another embodiment, a retention member 23, such as micro-beads are attached to a portion of the first struts 22 and are retained in central body 2. The plurality of first struts 22 are retained in central body 2 at a first position 71 in the central body 2. A second plurality of struts 24 are retained in central body 2 at a second position 72 in the central body 2 according to similar mechanical means. The actuator assembly 32 actuates the plurality of side arrays 17. In one embodiment, the actuator assembly 32, for the side arrays 17 includes at least two struts 22.

The plurality of side arrays 17 is actuated by a plurality of stylets 16 to deploy a plurality of flat electrodes 18. The side stylets 16 are connected to a plurality of struts 22 and 24 through flexural connectors 19 and 26. The plurality of side arrays 17 are actuated by manipulating the plurality of non-removable side stylets 16 relative to central body 2, both of which are connected to the clinician's control device (not shown). The deployable electrode apparatus 1 can be removed by holding the side stylet 16 while retracting the fixed electrode array 8 on the central body 2 to fold the side electrode arrays 17 in the stowed position for removal, so the deployable electrode apparatus 1 can be more easily removed from the spinal space.

If the side stylets 16 are attached to the inner wall or embedded within the walls of the outer sheath 20, then the procedure to position the deployable electrode apparatus 1 includes the steps of positioning the central body 2 as desired with the mid-line stylet. 4. Then the clinician holds the outer sheath 20 steady and pulls the central body 2 proximally (toward the clinician) to deploy the plurality of side electrode arrays 17. If the clinician wishes to retract the plurality of side electrode arrays 17, the clinician continues pulling the central body 20 (toward the clinician) proximally until the plurality of side electrode 18 are against either side of the central body 2 as shown in FIG. 1.

Figure 10:
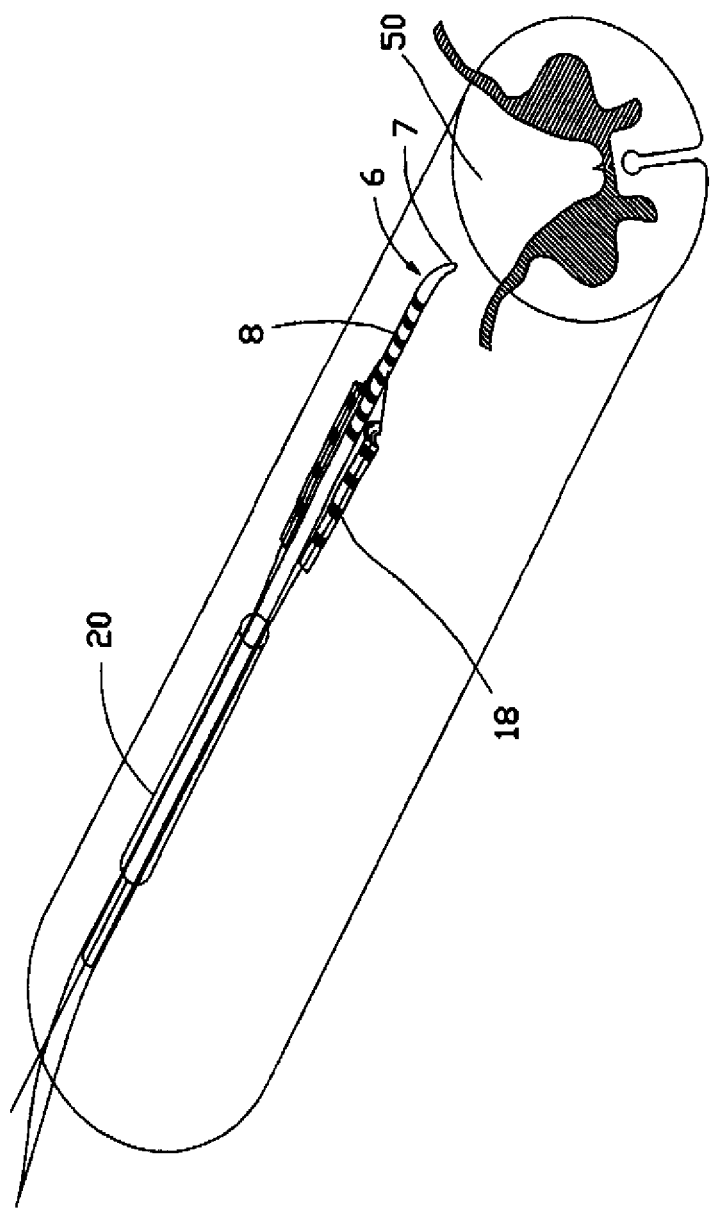
FIG. 10 shows a view illustrating the installation of the deployable electrode apparatus into a patient's spine in the retracted form.
Figure 11:
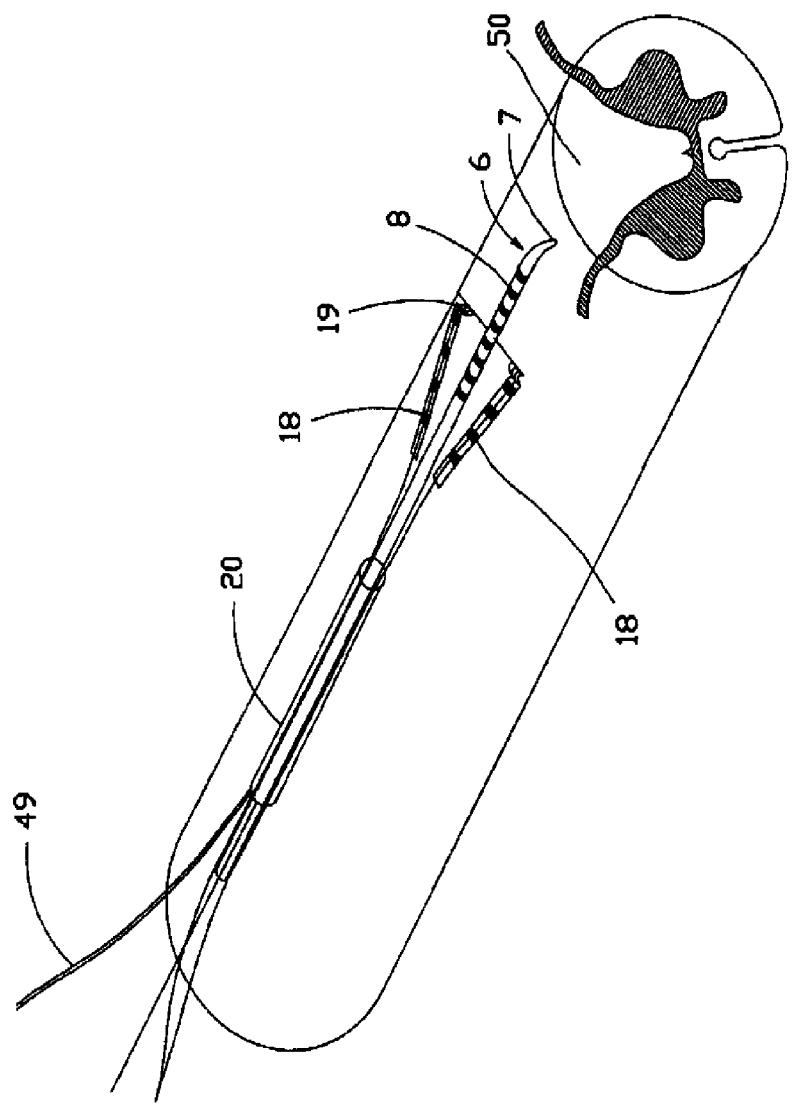

Now referring to FIGS. 10-11, once the distal end 6 of the deployable electrode apparatus 1 is in the epidural space 50, as deployed out of the Tuohy needle, it is positioned by advancing mid-line stylet 4 forward. Then the electrodes 18 on the side electrode arrays 17 are actuated, i.e. positioned to provide the desired therapy. Together with the fixed electrode array 8, electrical stimulation can be provided to the patient with deployable electrode apparatus 1.

The deployable electrode apparatus 1 can be used in other medical procedures that require electrical stimulation such as, peripheral nerve, ganglia, intra-spinal, sacral root, intra-ventricular cerebral, intrathecal or subdural spaces, and muscles including cardiac muscles.

INCORPORATION BY REFERENCE

All patents, published patent applications, and other references disclosed herein are hereby expressly incorporated by reference in their entireties by reference.

EQUIVALENTS

The functions of several elements may, in alternative embodiments, be carried out by fewer elements, or a single element. Similarly, in some embodiments, any functional element may perform fewer, or different, operations than those described with respect to the illustrated embodiment. Also, functional elements (e.g., modules, databases, computers, clients, servers and the like) shown as distinct for purposes of illustration may be incorporated within other functional elements, separated in different hardware or distributed in a particular implementation.

While certain embodiments according to the invention have been described, the invention is not limited to just the described embodiments. Various changes and/or modifications can be made to any of the described embodiments without departing from the spirit or scope of the invention. Also, various combinations of elements, steps, features, and/or aspects of the described embodiments are possible and contemplated even if such combinations are not expressly identified herein.

The invention claimed is:

1. A deployable electrode apparatus comprising:
   a fixed electrode array made of a central body having an open proximal and closed distal end, a mid-line stylet removable through the open proximal end, a fixed electrode array positioned on said central body; and
   a flat deployable electrode array; wherein said deployable electrode array is actuated by at least two struts, each of said struts having a first and second end, the central body of the apparatus configured to retain said first end of each said at least two struts;
   at least two side electrode arrays, each of said side arrays flexurally connected to the second end of each of the struts, said side arrays connected to at least one stylet, said at least one stylet.

2. The apparatus of claim 1 further comprising a sheath configured to retain said deployable electrode array in the retracted form.

3. The apparatus of claim 1 further comprising a retention member disposed in said central body to retain said first end of said at least two struts.

4. The apparatus of claim 1 wherein said retention member is a micro bead.

5. The apparatus of claim 4 wherein a washer is positioned between said micro bead and said central body.

6. The apparatus of claim 1 wherein said side arrays have an electrical support and said electrical support is connected to said stylet.

7. The apparatus of claim 1 wherein said plurality of first struts are retained in the central body at a first position and a second plurality of struts are retained in central body at a second position.

* * * * *

UNITED STATES PATENT AND TRADEMARK OFFICE
CERTIFICATE OF CORRECTION

PATENT NO. : 8,649,880 B1
APPLICATION NO. : 13/526089
DATED : February 11, 2014
INVENTOR(S) : Parker, Jr.

Page 1 of 1

It is certified that error appears in the above-identified patent and that said Letters Patent is hereby corrected as shown below:

In the Claims

In Claim 1, at Col 8, lines 6-7 the words "at least one stylet" are duplicated. Delete one duplication of the words and insert the following claim:

-- A deployable electrode apparatus comprising:
a fixed electrode array made of a central body having an open proximal and closed distal end, a mid-line stylet removable through the open proximal end, a fixed electrode array positioned on said central body; and a flat deployable electrode array; wherein said deployable electrode array is actuated by at least two struts, each of said struts having a first and second end, the central body of the apparatus configured to retain said first end of each said at least two struts;
at least two side electrode arrays, each of said side arrays flexurally connected to the second end of each of the struts, said side arrays connected to said at least one stylet. --

Signed and Sealed this
Sixth Day of May, 2014

Michelle K. Lee
*Deputy Director of the United States Patent and Trademark Office*